United States Patent
Lutz et al.

(10) Patent No.: US 8,603,091 B2
(45) Date of Patent: Dec. 10, 2013

(54) PELVIC AND SCAPULAR BONE PLATE AND METHOD FOR IMPLANTATION

(75) Inventors: Christian Lutz, Mönkeberg (DE); Jakob Kemper, New York, NY (US)

(73) Assignee: Stryker Trauma AG (CH)

( * ) Notice: Subject to any disclaimer, the term of this patent is extended or adjusted under 35 U.S.C. 154(b) by 69 days.

(21) Appl. No.: 13/040,722

(22) Filed: Mar. 4, 2011

(65) Prior Publication Data
US 2012/0226279 A1    Sep. 6, 2012

(30) Foreign Application Priority Data

Mar. 4, 2011  (EP) .................................... 11157015

(51) Int. Cl.
*A61B 17/80* (2006.01)
*A61B 17/88* (2006.01)

(52) U.S. Cl.
USPC .............. 606/70; 606/281; 606/284; 606/286

(58) Field of Classification Search
USPC ...................... 606/70–71, 280–299, 902–906
See application file for complete search history.

(56) References Cited

U.S. PATENT DOCUMENTS

| | | | |
|---|---|---|---|
| 2,580,821 A * | 1/1952 | Toufick | 606/282 |
| 4,029,091 A * | 6/1977 | von Bezold et al. | 606/33 |
| 4,403,607 A * | 9/1983 | Woo et al. | 606/70 |
| 4,454,876 A | 6/1984 | Mears | |
| 4,800,874 A | 1/1989 | David et al. | |
| 5,006,120 A * | 4/1991 | Carter | 606/71 |
| 5,326,367 A | 7/1994 | Robioneck et al. | |
| 5,690,631 A | 11/1997 | Duncan et al. | |
| 5,746,742 A * | 5/1998 | Runciman et al. | 606/86 B |
| 5,941,878 A | 8/1999 | Medoff | |
| 6,004,353 A | 12/1999 | Masini | |
| 6,306,173 B1 | 10/2001 | Masini | |

(Continued)

FOREIGN PATENT DOCUMENTS

| | | |
|---|---|---|
| DE | 3839859 A1 | 8/1989 |
| EP | 1897509 A1 | 3/2008 |
| FR | 590290 A | 6/1925 |
| FR | 2906126 A1 | 3/2008 |

(Continued)

OTHER PUBLICATIONS

Grade-5 (6AI-4V-3.7165-R56400) Titanium. Material Property Database, accessed on Sep. 19, 2012. <http://www.makeitfrom.com/material-data/?for=Grade-5-6AI-4V-3.7165-R56400-Titanium>.*

(Continued)

*Primary Examiner* — Eduardo C Robert
*Assistant Examiner* — Marcela I. Shirsat
(74) *Attorney, Agent, or Firm* — Lerner, David, Littenberg, Krumholz & Mentlik, LLP

(57) ABSTRACT

The invention relates to a pelvic or scapular bone plate implant having a planar or curved outer frame portion. The frame has a surface which can be aligned with a surface of a bone to which the bone plate is to be implanted. The plate has a flap portion, the outer frame portion at least partially surrounds the flap portion such that the bone contacting surface the flap portion is located within the outer boundary of the frame portion. The flap portion is connected with the outer frame portion via a material interconnection which allows the flap to be bent with respect to the frame. A method for implanting such a bone plate implant is also taught.

22 Claims, 13 Drawing Sheets

(56) References Cited

U.S. PATENT DOCUMENTS

| | | | |
|---|---|---|---|
| 6,440,131 B1 | 8/2002 | Haidukewych | |
| 6,840,959 B2 | 1/2005 | Treacy et al. | |
| 2002/0042654 A1 | 4/2002 | Masini | |
| 2003/0105464 A1* | 6/2003 | Schreurs et al. | 606/72 |
| 2004/0097936 A1* | 5/2004 | Ebid | 606/69 |
| 2004/0186477 A1* | 9/2004 | Winquist et al. | 606/72 |
| 2005/0165401 A1 | 7/2005 | Pack | |
| 2007/0083204 A1* | 4/2007 | Sidebotham | 606/69 |
| 2009/0275987 A1* | 11/2009 | Graham et al. | 606/280 |
| 2011/0046681 A1* | 2/2011 | Prandi et al. | 606/286 |

FOREIGN PATENT DOCUMENTS

| | | | |
|---|---|---|---|
| JP | 2004-154480 A | 6/2004 | |
| WO | 01/78616 A1 | 10/2001 | |
| WO | WO 2010037985 A1 * | 4/2010 | A61B 17/80 |

OTHER PUBLICATIONS

Acumed, Locking Scapula Plate System, 2008.
Stryker Trauma AG, SPS Matta Pelvic System, 2006.
European Search Report, EP 1157015, dated Aug. 4, 2011.

* cited by examiner

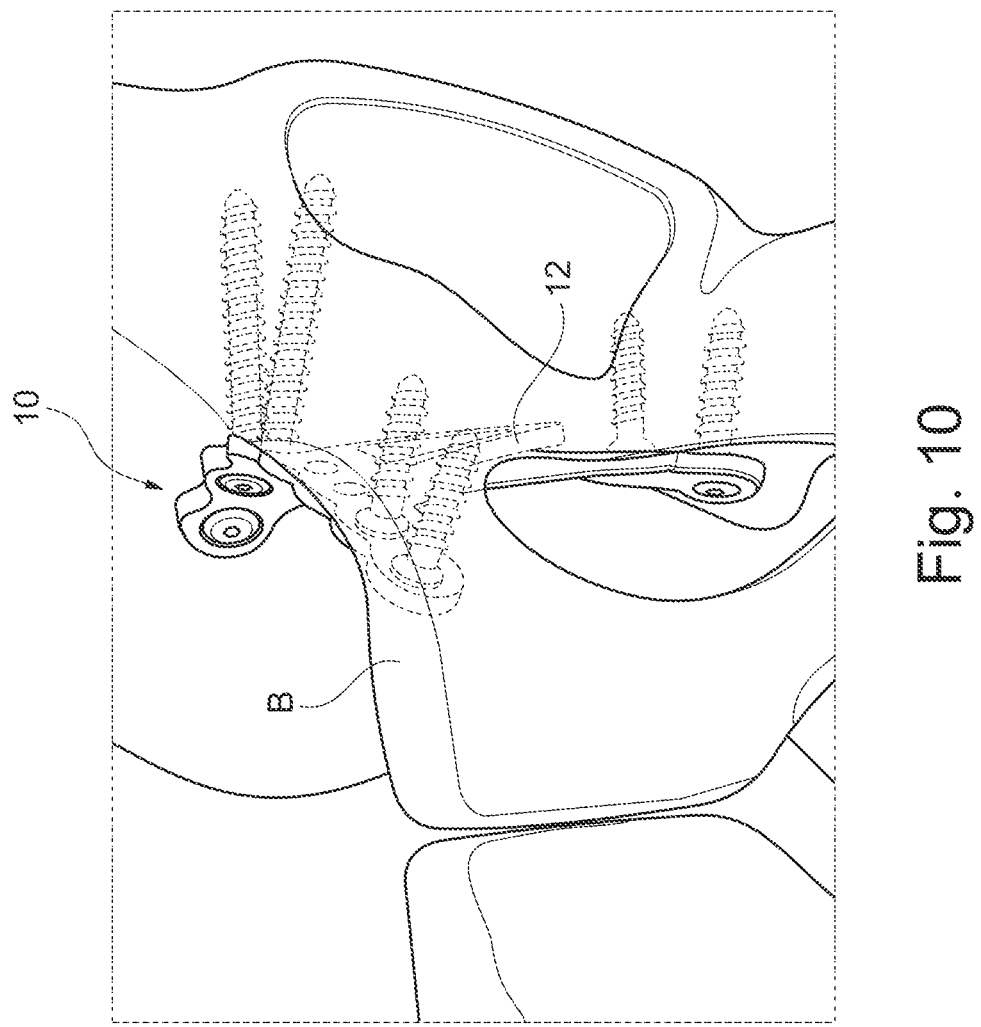

PELVIC AND SCAPULAR BONE PLATE AND METHOD FOR IMPLANTATION

CROSS-REFERENCE TO RELATED APPLICATIONS

This application claims the benefit of EPO Provisional Application EP11157015, filed on Mar. 4, 2011, entitled "Pelvic and Scapular Bone Plate and Method for Implantation," the contents of which is incorporated in its entirety by reference herein.

BACKGROUND OF THE INVENTION

The invention relates to a pelvic and scapular bone plate implant and a surgical method for implanting such a pelvic and scapular bone plate implant.

Surgical methods are known for reconstructing a patient's anatomy after a bone fracture. These procedures rely on the surgeon's use of metallic plates or meshes which are screwed to a fractured bone in order to reset comminuted areas of the fractured bone. These plates may carry the load of the comminuted area of the bone. Due to the rigidity of the plate, the fractured bone can heal in the proper position, because motion is minimized. These strong plates must usually be contoured to the surface shape of the bone. An example for a fixation plate is shown in U.S. Pat. No. 4,454,876 which discloses a pelvic fixation plate and method of implanting the same. Also see the Matta Pelvic System sold by Stryker® Corporation. However, with the plates from the state of the art, especially with plates for larger surfaces, it can be very challenging to bend the plate correctly with respect to the anatomical region. A pressure on an inside shape can be achieved by contouring the plate beyond the bending extent required for the plate to touch the bone surface in that area, but it is very difficult for a surgeon to adjust the slope and this can lead to a suboptimal fit along the outer edges.

The quadrilateral surface of the pelvis is often affected by high impact pelvic fractures, because the femoral head is driven from the acetabulum through the quadrilateral surface towards the inner pelvis. This results in a comminuted fracture of the quadrilateral surface. Especially since the center of this wall between inner pelvis and acetabulum is very thin and has to be buttressed in order to re-establish the acetabular surface. However, under consideration of the above difficulties encountered when forming the known plates, there is potential for improvement in plates for buttressing contoured large-area bones.

BRIEF SUMMARY OF THE INVENTION

It is one aspect of the invention to provide a pelvis bone plate implant, a scapula bone plate implant, a surgical method for implanting the pelvis bone plate implant and a surgical method for implanting the scapula bone plate implant, in order to improve the buttressing of a fractured bone.

This aspect is achieved using a pelvic bone plate implant comprising: a frame portion having a surface which can conform to a surface of a pelvic bone to which the bone plate implant is to be implanted. A flap portion is partially attached to the outer frame portion with the frame portion at least partially surrounding the flap portion such that a bone contacting surface of the flap portion is located within an outer boundary of the frame portion. The flap portion is partially attached to the outer frame portion via a material interconnection and is bendable with respect to a surface defined by the frame portion. An angle of inclination ($\alpha$) of the flap portion defines the bending of the flap portion away from the frame-surface. The flap portion is adjustable relative to the frame-surface by plastically deforming a portion of the material interconnection between the flap portion and the frame portion. The flap portion may be pre-bent away from the frame portion surface with an angle of inclination ($\alpha$) relative to the frame-surface of between 10 and 20 degrees. Preferably both the frame portion and the flap portion are plastically deformable.

The bone plate implant may be formed from one piece of material wherein the boundary of the frame portion surrounds at least 80% of the circumference of the flap portion. Preferably the outer frame portion is a closed frame. The flap portion preferably is free of fixation apertures for receiving fasteners such as bone screws. The flap portion may be connected with the outer frame portion via material bridges. The outer frame portion may be provided with a plate segment projecting in a direction in parallel to an imaginary bending axis of the material interconnection. The frame portion can have a substantially triangular shape wherein the flap portion is also substantially triangular. The flap portion is separated from the frame portion in part by a slot or slots and the outer shape of the flap portion substantially corresponds to the inner shape of the outer frame portion. A plurality of apertures provided along the outer frame portion for fixing the bone plate implant. The material interconnection of the flap portion to the frame portion comprises a spring constant between 200 N/mm and 2400 N/mm.

A Scapular bone plate implant is also provided which comprises a planar or curved outer frame portion having a frame-surface which can be aligned to a bone-surface of a bone to which the scapula bone plate implant is to be implanted. Again a flap portion is provided. The outer frame portion at least partially surrounds the flap portion such that in the bone-surface, the flap portion is located within the outer dimensions of the outer frame portion. The scapular plate has similar features to the pelvic plate described above. The flap portion is connected with the outer frame portion via a material interconnection.

A surgical method for implanting the pelvis bone plate implant set forth above comprises pre-bending the outer frame portion according to the shape of the bone, pre-bending the flap portion towards an area of the bone to be buttressed, implanting the pelvis bone plate implant by fixing it to the pelvis. The pre-bending of the outer frame portion involves contouring the outer frame portion to the shape of the pelvis area to which the bone plate implant is to be applied. The flap portion is bent to an angle of inclination with respect to the frame portion between about 10° and 20°. The surgical method for implanting the scapula bone plate implant includes pre-bending the outer frame portion according to the shape of the bone, pre-bending the flap portion towards an area of the bone to be buttressed, implanting the scapula bone plate implant by fixing it to the scapula.

A method for fixing a fracture of a pelvic or scapular bone may comprise determining the size and location of the fractured bone and obtaining a bone plate of appropriate size having a frame portion having a surface which can conform to a surface of a bone to which the bone plate implant is to be implanted. A flap portion is partially attached to the outer frame portion with the frame portion at least partially surrounding the flap portion such that a bone contacting surface of the flap portion is located within an outer boundary of the frame portion. The flap portion is partially attached to the outer frame portion via a material interconnection and is bendable with respect to a surface defined by the frame portion. The fracture is reduced and the shape of the reduced fractured bone is determined. The flap portion is bent in a direction away from the frame. The frame portion of the bone plate is shaped to generally match the shape of the reduced fractured bone. The bone plate frame is mounted on the fracture in a manner which deflects the flap portion towards the frame. Preferably the flap portion is bent to an angle of inclination with respect to the frame portion between about 10° and 20°. A template may be used to determine the shape of the fractured area.

According to one aspect of the invention, there is provided a pelvic bone plate implant comprising a planar or curved outer frame portion having a frame-surface which can be aligned to a bone-surface of a bone to which the pelvic bone plate implant is to be implanted, and a flap portion, the outer frame portion at least partially surrounds the flap portion such that in the bone-surface the flap portion is located within the outer dimensions or perimeter of the outer frame portion, wherein the flap portion is connected with the outer frame portion via a material interconnection. The definitions given in this summary are valid throughout the entire specification. A "material interconnection" is a connection in which the connected parts are fixed to each other by atomic or molecular forces. These are non-detachable connections which can only be separated by destruction of the connection. Preferably, the material interconnection is integrally formed. More preferably, the material interconnection is formed monolithically. Thus, a bone plate made from a single stamped metal plate would exhibit such properties. The advantage of such a bone plate implant is that the outer frame portion functions as the stabilizing, supporting structure, whereas the flap portion supports the comminuted fractured area in the center of the plate. Due to the provision of the central flap portion and the surrounding outer frame portion, these parts may be shaped, formed and oriented differently according to the fracture and the shape of the bone.

According to one aspect of the invention, an angle of inclination of the flap portion away from the frame-surface is adjustable relative to the frame-surface by plastically deforming a portion of the bone plate implant. The deformed portion is preferably the material interconnection, but could also be the outer frame portion and/or the flap portion or only certain areas of the outer frame portion and/or the flap portion. For deforming the portion, preferably hand force of a surgeon is sufficient. This also allows that according to the fracture of the comminuted area or the bone surface, the angle of inclination of the flap portion can be adjusted such that it supports the comminuted area or, if the angle of inclination is large enough, it acts with a specific pressure or spring force towards the comminuted area in the center of the plate.

According to another aspect of the invention, the flap portion is pre-inclined away from the frame-surface with an angle of inclination relative to the frame-surface. The bone plate implant according to this embodiment is already provided by the manufacturer in a pre-formed shape, in which the flap portion is already inclined relative to the frame-surface. This embodiment has the above mentioned advantages.

According to a further aspect of the invention, the outer frame portion and/or the flap portion is plastically deformable. The advantage of such a bone plate implant is that the shape of the outer frame portion and/or the shape of the flap portion can be adapted or contoured more easily to the bone-surface where the bone plate implant is to be attached. This plastic deformation can preferably be accomplished by the surgeon using only hand force. Alternately bending instruments can be provided.

According to a yet further aspect of the invention, the bone plate implant is formed monolithically from one piece of for example implant grade stainless steel. This way, the bone plate implant can be manufactured comparatively inexpensively and the material interconnection can be formed easily without encountering any jointing problems.

Preferably, the outer frame portion surrounds, in the bone-surface contacting area, at least 80% of the circumference around the flap portion. More preferably, the outer frame portion is a closed frame. The more the outer frame portion is closed, the more stabilizing and rigid it will be.

According to a yet further aspect, the flap portion is free of fixation apertures for inserting fastening means although such bone screw openings can be provided. As the flap portion is intended to support the quadrilateral surface which is an area being often affected by high impact pelvic fractures, it is difficult to insert fastening means, e.g. bone screws or nails, into the bone. The design of this bone plate implant makes it possible to omit those fastening means in the central area.

According to a yet further aspect of the invention, the flap portion is connected with the outer frame portion via the material interconnection in the form of two material bridges. This way, the bending characteristics like plastic deformation characteristics and the elasticity can be pre-defined by dimensioning the cross-sections of the material bridges.

According to a yet further aspect of the invention, the outer frame portion is provided with a projection projecting in a direction in parallel to an imaginary bending axis of the material interconnection. The "bending axis" is the imaginary line about which the flap portion is rotated when the flap portion is bent by the surgeon by deforming the material interconnection. Due to the flap projection, the segment of the outer frame portion, which is attached to the pelvic brim, can carry a larger force for stabilizing the bone plate implant and thus for stabilizing the comminuted area. "Projecting in a direction in parallel to" does not require that the longitudinal axis of the projection and the bending axis are parallel, but only that the material of the projection extents in a direction in parallel to the bending axis.

According to a yet further aspect of the invention, the outer frame portion and/or the flap portion is substantially triangular. The term "substantially triangular shape" does not require a precise triangle, but also may include also shapes which have rounded corners and triangular shapes, the sides of which are not precisely straight.

According to a yet further aspect of the invention, the outer shape of the flap portion substantially corresponds, in its bone contacting surface, to the inner shape of the outer frame portion. If these shapes correspond well to each other, the area to be buttressed is covered better without the occurrence of large opened areas which would not contribute in supporting the comminuted area. The "outer shape of the flap portion" is the contour of the radially outer edge of the flap portion. The "inner shape of the outer frame" is the contour of the radially inner edge of the outer frame portion. Along the outer edge of the flap portion in a bone-surface, the distance between the outer edge of the flap portion and the opposing inner edge of the outer frame portion is preferably constant, or substantially constant.

According to a yet further aspect of the invention, the pelvis bone plate implant further comprises a plurality of apertures provided along the outer frame portion for fixing the bone plate implant. These apertures function as holes for positioning and holding fastening means, e.g. bone screws or nails, in order to fasten the bone plate implant to the bone.

According to a yet further aspect of the invention, the flap portion comprises a spring constant between 200 N/mm and 2400 N/mm. Preferably, the spring constant is 600 N/mm to 1200 N/mm, and more preferably the spring constant is 700

N/mm to 1000 N/mm. When bending the material interconnection beyond an extent with would be required for the flap portion to touch the bone, a spring force is acting against the comminuted fractured area. The pressure force acting on the comminuted area can be adjusted by the magnitude of bending or pre-forming of the angle of inclination. Providing the flap portion with a spring constant within the mentioned range avoids a repositioning of the fractured bone.

According to an aspect of the invention, there is provided a scapula bone plate implant comprising a planar or curved outer frame portion having a frame-surface which can be aligned to a bone-surface of a bone to which the scapula bone plate implant is to be implanted, and a flap portion, the outer frame portion surrounding the flap portion at least partially such that in the bone-surface, the flap portion is located within the outer dimensions of the outer frame portion, wherein the flap portion is connected with the outer frame portion via a material interconnection. This scapula bone plate can comprise the features and further developments described above in connection with the pelvis bone plate. This scapula bone plate implant inherits the same advantages as the pelvis bone plate implant described above, therefore repetitions can be omitted at this point.

These advantages can also be realized by other aspects of the invention according to which a surgical method for implanting the above pelvis bone plate implant is provided. The method comprises the steps of pre-bending the outer frame portion according to the shape of the bone, pre-bending the flap portion towards an area of the bone to be buttressed, and implanting the pelvic bone plate by fixing it to the pelvis.

These advantages can also be realized by a further aspect of the invention according to which a surgical method for implanting the above scapula bone plate implant is provided. The method comprises the steps of pre-bending the outer frame portion according to the shape of the bone, pre-bending the flap portion towards an area of the bone to be buttressed, and implanting the scapula bone plate implant by fixing it to the scapula.

According to a yet further aspect of the invention, the pre-bending of the outer frame portion involves contouring the outer frame portion to the shape of the bone area to which the bone plate implant is to be applied.

These and other aspects of the invention will be apparent from and elucidated with reference to the embodiments described hereafter.

BRIEF DESCRIPTION OF THE DRAWINGS

FIG. 10 is an enlarged three-dimensional view of FIG. 9;

DETAILED DESCRIPTION

Figure 1:
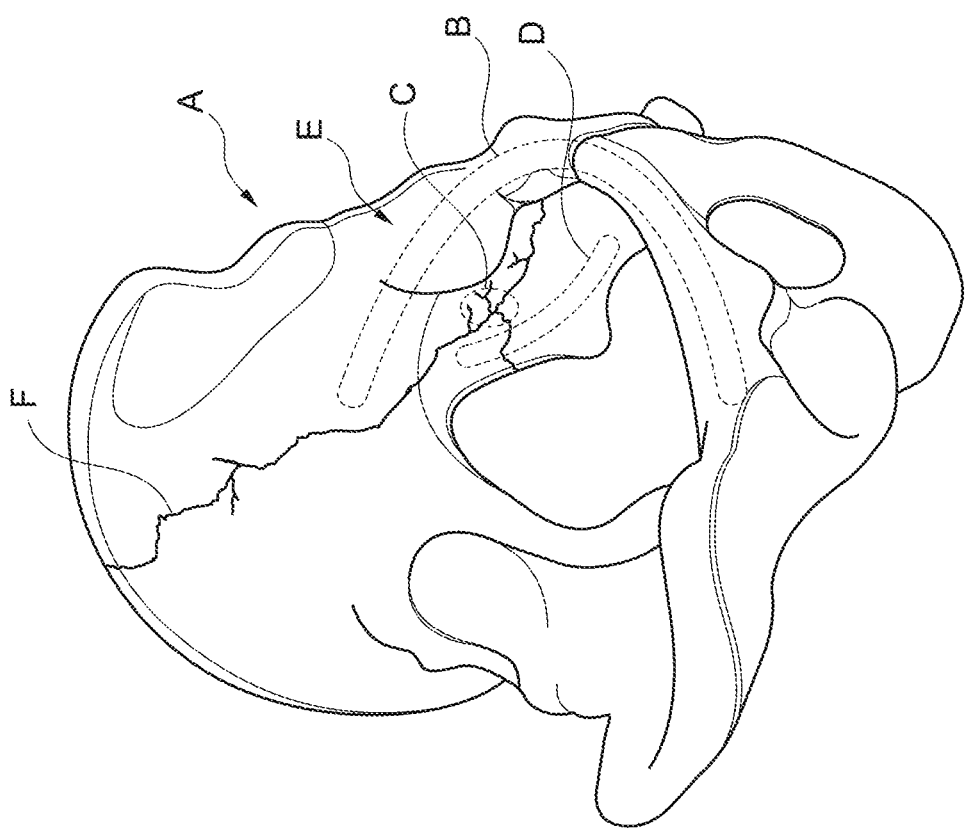
FIG. 1 is a three-dimensional view of a human pelvis from a perspective looking inclined downwards from the right side of the pelvis to the left side of the pelvis presented for explanatory reasons.

FIG. 1 is a three-dimensional view of a human pelvis A from a perspective looking inclined downwards from the right side of the pelvis to the left side of the pelvis. In this Figure, the pelvic brim is roughly framed with a dashed line and indicated with reference numeral B, the quadrilateral surface is roughly encircled with a dashed line and indicated with reference numeral C, the anterior column is roughly framed with a dashed line and indicated with reference numeral D, and the acetabulum is indicated with reference numeral E. Further, an exemplary fracture F is shown, which runs all across the pelvis A and passes through the quadrilateral surface C. Of course, this fracture F is only an example, and other fractures are likely in which primarily the quadrilateral surface C is comminuted.

Figure 2:
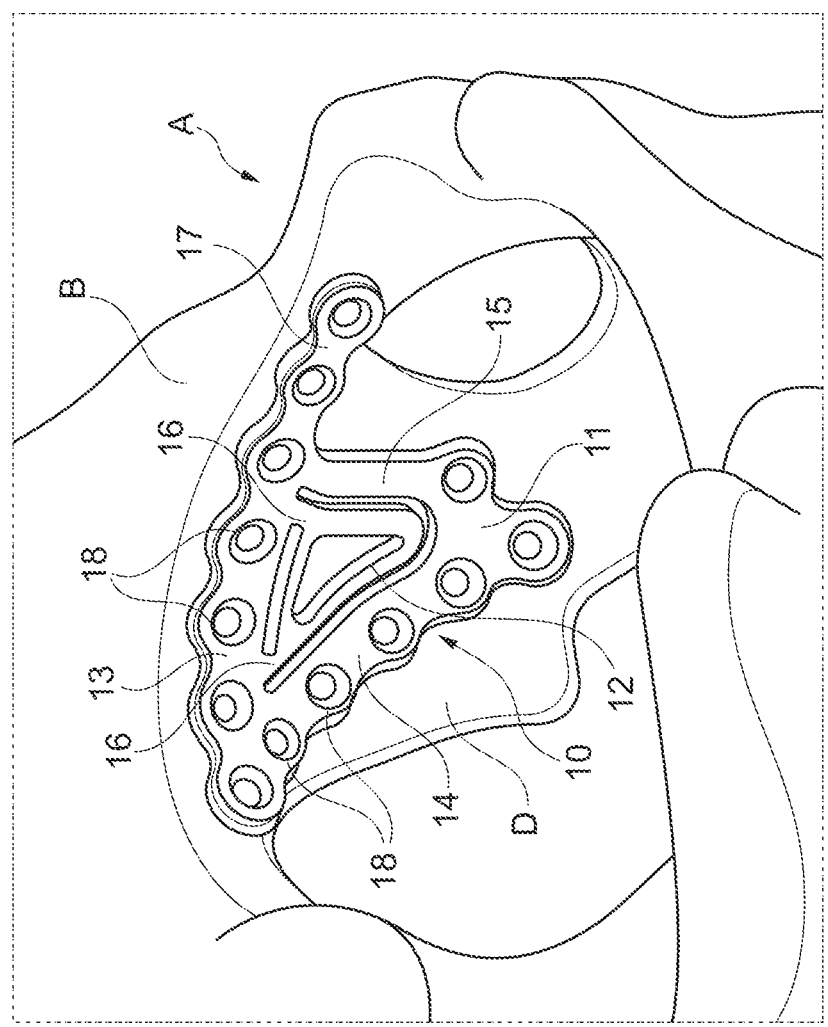
FIG. 2 is a three-dimensional view of a bone plate implant having an outer frame and a central flap portion according to an embodiment of the invention, the bone plate implant being located at the implanting position of a human pelvis.
Figure 3:
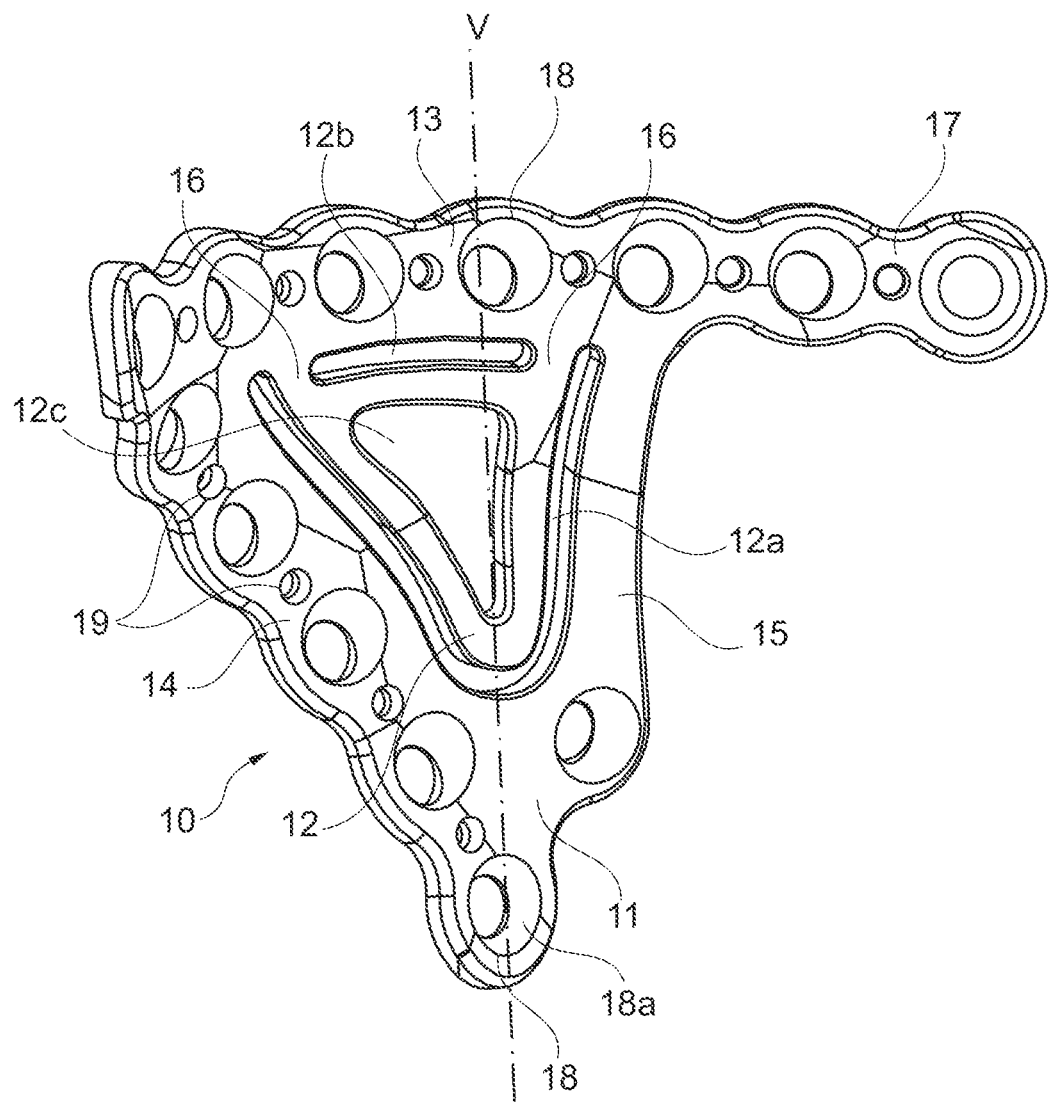
FIG. 3 is a left three-dimensional side view of the bone plate implant.
Figure 4:
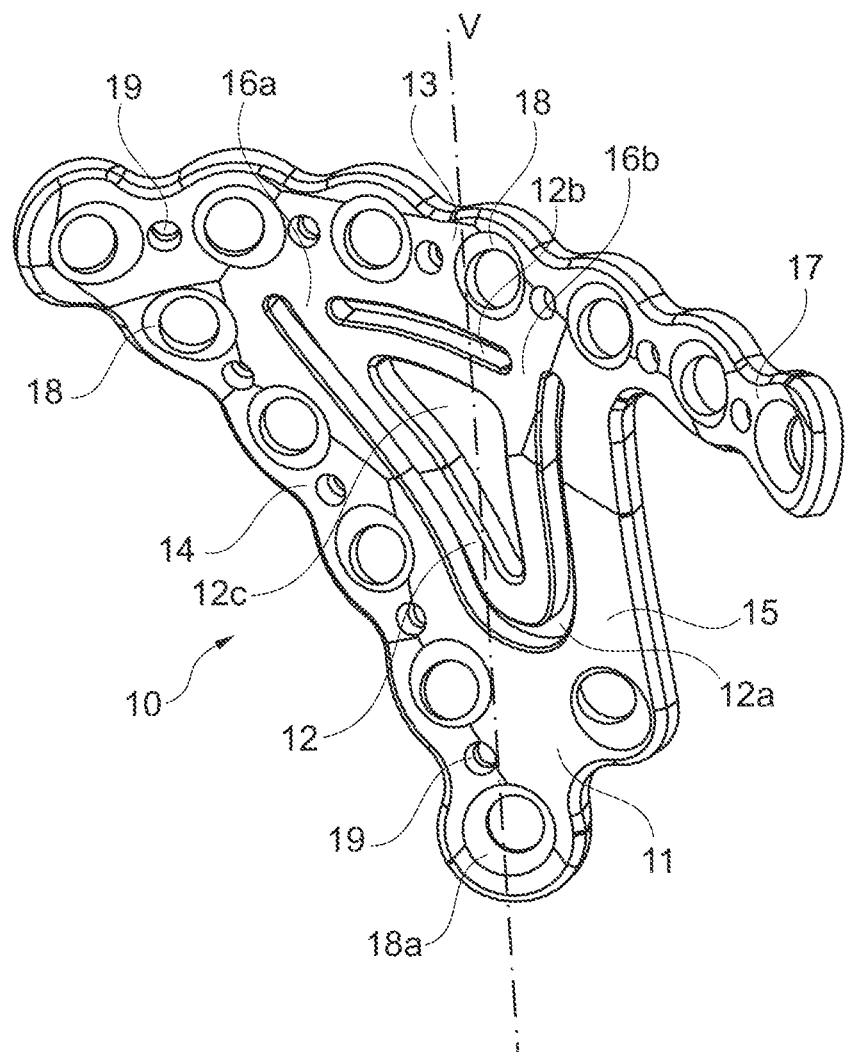
FIG. 4 is a right three-dimensional side view of the bone plate implant.

FIG. 2 shows a bone plate implant 10 according to an embodiment of the invention, the bone plate implant 10 being located at the implanting position of a human pelvis A, whereas FIGS. 3 and 4 show this bone plate implant 10 in different three-dimensional views. Alternatively to the pelvis A, the bone plate implant 10 could also be implanted to a scapula (shoulder blade). These bone plates may come in more than one size and be supplied in kit form.

The bone plate implant 10 is a flat, large-area plate for covering major parts of the quadrilateral surface C of the pelvis A. In other words, the thickness of the bone plate implant 10 is comparatively small versus a dimension in the direction of the surface which is supposed to contact the bone. The thickness is preferably 2 to 5 mm.

The bone plate implant 10 basically comprises an outer frame portion 11 and an inner flap portion 12. The outer frame portion 11 and the flap portion 12 are preferably monolithically formed of titanium, preferably the type Ti6Al4V, or formed of implant grade stainless steel, preferably the type 1.4441. In case of titanium, the Young's modulus would be about 110000 N/mm$^2$, and in case of implant grade stainless steel, the Young's modulus would be about 210000 N/mm$^2$. The outer frame portion 11 has a substantially triangular shape, wherein the three sides of the triangular shape are formed by flat stripe-shaped segments 13, 14 and 15, monolithically forming the outer frame portion 11. The outer frame portion 11 is preferably a closed frame, but could also be opened. However, if it opened the flap portion 12 should still be located within the outer dimensions of the outer frame portion 11 (in a state in which the bone plate implant 11 is attached to the bone such that both, the outer frame portion 11 and the flap portion 12 are touching the bone and are conform to the bone-surface). The outer frame portion 11 can be plastically deformed, or in other words rigidly shaped, and fixed to the anatomically carrying structure of the pelvis. After being deformed, the outer frame portion 11 still has some elasticity. On one hand, the magnitude of elasticity has to be such that the outer frame portion 11 is rigid enough for appropriately fulfilling the supporting function, i.e. rigid enough for sufficiently stabilizing the bone plant implant 10 and for sufficiently stabilizing the bone to be buttressed. On the other hand, the remaining elasticity should be such that the outer frame portion 11 adapts its contour with the contour of the bone surface on which the outer frame portion 11 is implanted. The forming of the outer frame portion 11 can preferably be accomplished by hand, or alternatively by appropriate bending tools, by the surgeon during or shortly before the surgery or implantation. The load imparted from the bone plate implant 10 to the pelvis A is carried by the anterior column D and the pelvic brim B of the pelvis A. Thus, the segment 14 of the outer frame portion 11 is attached to the anterior column D of the pelvis A and referred to as anterior column segment 14, and the segment 13 is attached to the pelvic brim B and referred to as pelvic brim segment 13. This outer frame portion 11 surrounds, in a bone-surface, the flap portion 12 which is formed as a substantially triangular frame, wherein the three sides of this triangular shape are formed by flat stripe-shaped segments separated from the remainder of the bone plate implant 10 by slots 12a, 12b.

The flap portion 12 may have a central opening 12c. The flap portion 12 is preferably monolithically formed. Also, the shape of the flap portion 12 can be plastically deformed, preferably by hand force, or alternatively by appropriate bending tools. After being deformed the flap portion 12 still has some elasticity. On one hand, the magnitude of elasticity is preferably such that the flap portion 12 is rigid enough for appropriately fulfilling the supporting function, i.e. rigid enough for sufficiently supporting the comminuted bone area. On the other hand, the remaining elasticity should be such that the flap portion 12, when an angle of inclination α (see FIGS. 11c and 12b) between the flap portion 12 and the outer frame portion is larger as would be necessary in order to abut the flap portion 12 to the comminuted bone area, exhibits a suitable spring force towards the comminuted bone area. On one side of its triangular shape, the flap portion 12 is, preferably monolithically, connected with the outer frame portion 11, namely to the pelvic brim segment 13. In particular, the flap portion 12 is connected at two corners of its triangular shape with the pelvic brim segment 13. This material interconnection 16 is realized by extending the two other sides (the sides other than the connected side) of the triangular shape of the flap portion 12 along the direction of the frame-surface beyond the outer border of the connected side to reach the inner side of the outer frame portion 11. This way, the material interconnection 16 is in the form of two material bridges 16a, 16b connecting the outer frame portion 11 and the flap portion 12, wherein the cross-sectional area of the material bridges 16a, 16b is substantially the same as cross-sectional area of the individual segments of the flap portion 12 which surrounds opening 12c. Preferably, the angle of inclination α of the flap portion is adjustable relative to the outer frame portion by plastically deforming the material interconnection 16, i.e. by rotating the flap portion 12 about a bending axis. By defining the cross-sectional area of the material bridges, the plastic and/or elastic characteristics can be adjusted appropriately.

There are several possibilities of forming the material interconnection 16. As already mentioned, the cross-sectional area can be adapted, e.g. the width of the material bridges 16a, 16b can be changed. Further, the thickness of the material bridges can be varied by forming one or more cuts (not shown) into the material interconnection on the side facing towards the bone to be buttressed and/or the side facing opposite thereto, the cuts running substantially in a direction in parallel to the pelvic brim segment 13. Also, only a single material bridge can be formed and the material bridge can be weakened by forming in cuts, holes, through holes, blind holes, or the like. Of course, the bending axis runs through all the material bridges. Along the bending axis and in between the material bridges, the bone plate implant 10 slot 12b is free of material of the bone plate implant, i.e. there is an opening or openings. There is neither material from the outer frame portion 11 nor from the flap portion 12 crossing the bending line, in between the material bridges 16a, 16b, except from the material bridges themselves.

Further, the outer frame portion 11 is provided with a projection 17 projecting from the pelvic brim B in a direction in parallel to the side of the triangular shape of the flap portion 12, which is connected with the outer frame portion 11. Or in other words, the pelvic brim segment 13 projects further beyond the triangular base shape of the outer frame portion 11 in a direction away from the anterior column segment 14, preferably by 25 to 35 mm from the outer edge of segment 15.

The anterior column segment 14 and the pelvic brim segment 13 are provided with a plurality of large apertures 18, only some of which are indicated in the Figures with reference signs. The large apertures 18 are provided along the entire length of the anterior column segment 14 and the pelvic brim segment 13 in substantially equal intervals. In between the large apertures 18 there are provided small apertures 19, only some of which are indicated in the Figures with reference signs. Preferably, in between every two adjacent large apertures 18, there is provided one small aperture 19. The centers of the holes 18 and 19 are positioned substantially on the longitudinal centerline of the anterior column segment 14 and the pelvic brim segment 13. Moreover, in the segment 15, at the end area adjacent the anterior column segment 14, there is also provided a single large aperture 18. Each large aperture 18 is formed as countersunk hole, wherein the inside 18a is provided with a curved fillet instead of a conical chamfer, or in other words, the aperture is cut from one side with a spherical-shaped cutter. This results in each large aperture 18 having an inner diameter of 7.5 to 8 mm on one side and a diameter of 4.5 to 5.5 mm on the other (bone-contacting) side. The small apertures 19 are formed as countersunk holes provided with a chamfer. The inner diameter of the small apertures 19 is in between 2 and 3 mm. The large apertures 18 are used for inserting bone screws 20 for screwing the bone plate implant 10 to the bone, and the small apertures 19 are used for inserting Kirschner wires (K-wires) which are inserted for temporarily fixing and positioning the bone plate implant 10 relative to the bone before the screws 20 are inserted.

The outer shape of the bone plate implant 10, at least along the anterior column segment 14 and the pelvic brim segment 13, has a wave-like form along the outer edge of the bone plate implant 10 (along the surface of the radially outer edge) with the trough of the wave form being located in between two adjacent large fixing holes 18.

The concept of the bone plate implant 10 is to be rigidly connected to the load-carrying structures, namely the anterior column D and the pelvic brim B, and still easily facilitate a spring-loaded support of the comminuted area, most likely the quadrilateral surface C, in the center. This is accomplished with the flap portion 12. Prior to implanting the bone plate implant 10, the flap portion 12 can be pre-bent inwards towards the affected area by plastically deforming the material interconnection 16 which exhibit after being plastically deformed certain flexibility. As already mentioned above, by defining the cross-sectional area of the material bridges of this material interconnection 16, the plastic and/or elastic characteristics can be adjusted appropriately. These characteristics should preferably be adjusted such that the material interconnection 16 is rigid enough for appropriately fulfilling the supporting function, i.e. rigid enough for sufficiently supporting the comminuted bone area. On the other hand, the remaining elasticity should be such that the flap portion 12, when the angle of inclination $\alpha$ between the flap portion and the outer frame portion is larger as would be necessary in order to abut the flap portion 12 to the comminuted bone area, exhibits a suitable spring force towards the comminuted bone area. After the bone plate implant 10 is placed to the pelvic A, there is an elastic deformation of those areas generating a pressure on the center, or in other words, the flap portion 12 is bent back a certain degree towards its original unbent position. This causes a spring force acting on the comminuted area. The amount of the thus caused pressure can be adjusted by the surgeon by means of the extent of the plastic deformation he applies prior to implantation. Preferably, an equivalent spring constant at the tip of the flap portion 12, i.e. the end of the flap portion opposite from the material interconnection 16, is between 200 N/mm and 2400 N/mm. In order to realize the plastical formability and the remaining flexibility after the deformation of the bone plate implant, the material should comprise a Young's modulus in between 100000 N/mm$^2$ and 120000 N/mm$^2$, or in between 200000 N/mm$^2$ and 220000 N/mm$^2$.

The above mentioned equivalent spring constant was determined as follows. For calculating the equivalent spring constant at the tip of the flap portion 12, the width of the material bridges 16 is varied from 2 to 30 mm—this width is the total width of all material bridges (the sum of the widths of the individual material bridges). The thickness of the bone plate implant 10, and thus the thickness of the material bridges 16, is assumed to be 2.3 mm. With this minimal width of 2 mm and the maximum width of 30 mm, a resulting equivalent spring constant (at the tip of the flap portion 12) of 50 to 800 N/mm is calculated. In other words, the minimal width results in a spring constant of 50 N/mm and the maximal width results in a spring constant of 800 N/mm. If the thickness of the bone plate implant 10 is increased from 2.3 mm to 3 mm, a spring constant of 1600 N/mm results for a width of 30 mm.

From a biomechanical point of view, the static hip load can be assumed to be 800N. In a normal walking cycle, this value reaches the triple value of around 2400N. This load will not entirely act on the flap portion 12, because the outer frame portion 14 carries most of the load. Thus, if it is assumed, that around one-third of the load is transferred via the bone fragments underneath the flap portion 12 and the flap portion 12 must only allow 1 mm spring deflection (distance), a spring constant of 800 N/mm results, as in the calculational approach described in the previous paragraph. It is desirable to support not less than 25% and not more than three-times as much of the value of 800 N/mm. Thus, a range from 200 N/mm to 2400 N/mm results, with a minimal spring constant of 200 N/mm and a maximal spring constant of 2400 N/mm. This biomechanical approach is the preferred way of determining the spring constant range.

In the following description of the Figures, only some reference signs are provided for reasons of clarity. However, the above description in connection with the previous Figures apply accordingly.

Figure 5:
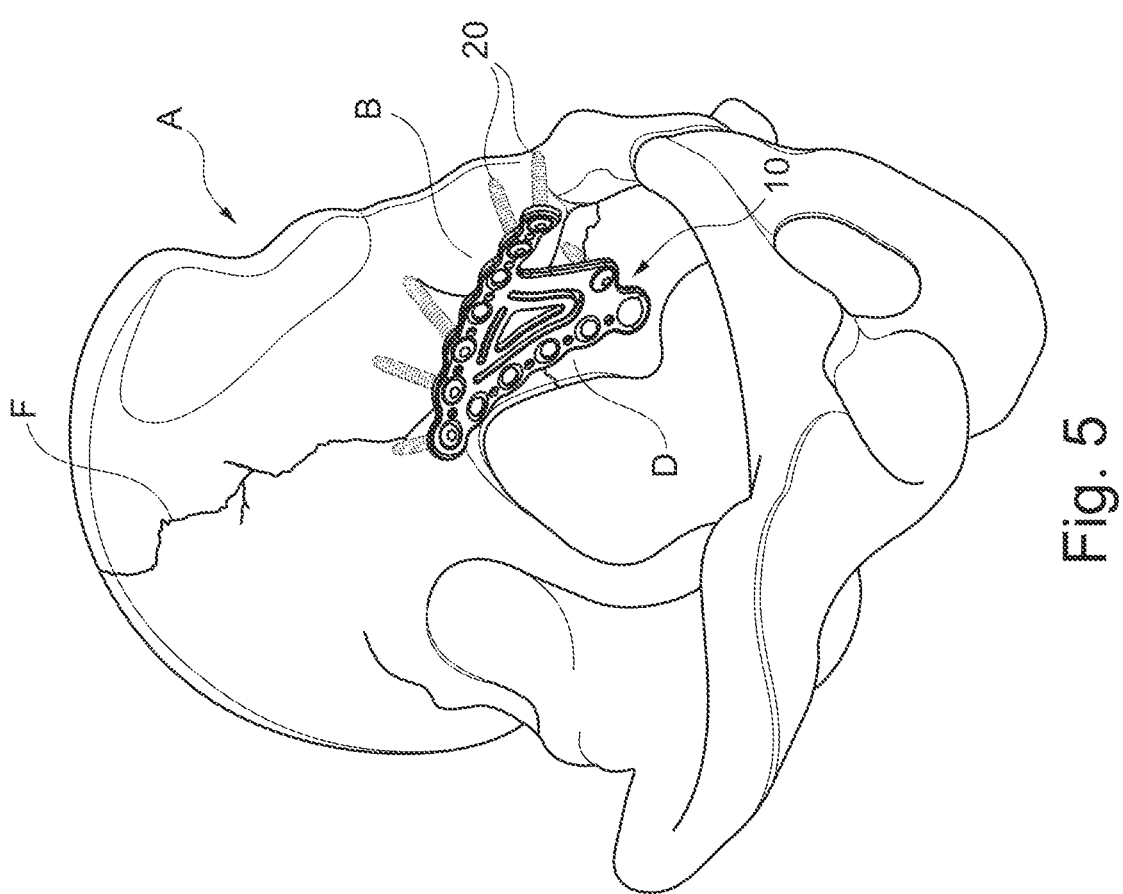
FIG. 5 is a three-dimensional view of a human pelvis of FIG. 1 with the implanted bone plate implant with the flap portion having an angle of inclination of 0°, the view is shown from a perspective looking inclined downwards from the right side of the pelvis to the left side of the pelvis.
Figure 6:
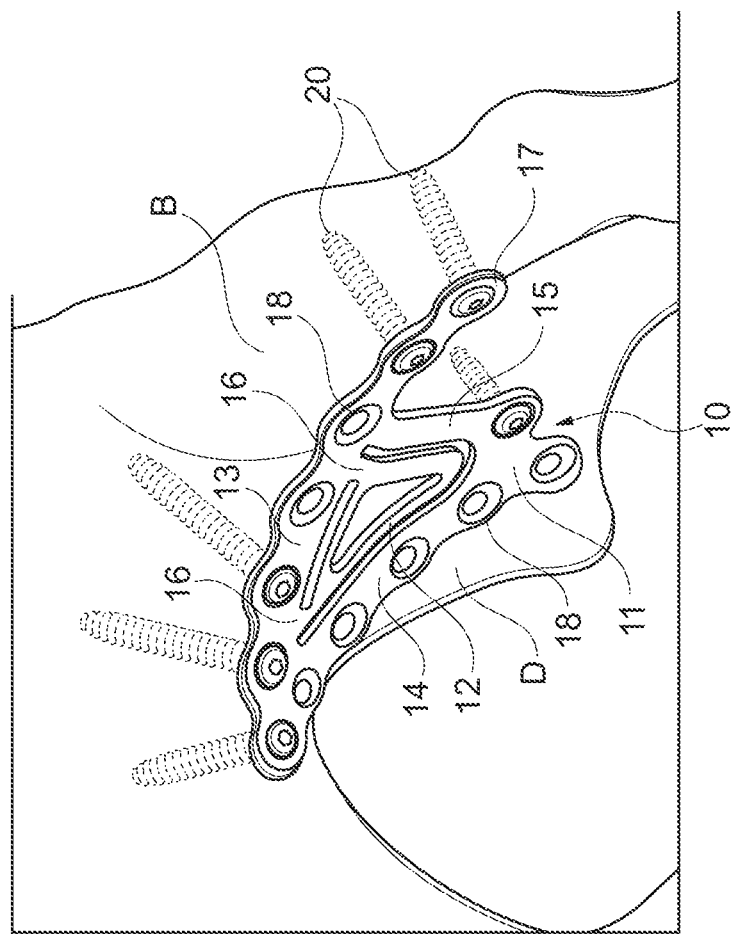
FIG. 6 is an enlarged three-dimensional view of FIG. 5.

FIG. 5 is a three-dimensional view of a human pelvis A with the implanted bone plate implant 10, looking inclined downwards from the right side of the pelvis A to the left side of the pelvis A. FIG. 6 is an enlarged three-dimensional view of FIG. 5. As shown in the Figures, the bone plate implant 10 is attached to the pelvis A by means of six bone screws 20 inserted through the large apertures 18, only two of which are provided with a reference sign. The bone screws 20 are provided in different length and are chosen by the surgeon according to the thickness of the bone, a specific bone screw 20 is screwed into. From the plurality of large apertures 18, not necessary all of them have to be provided with a bone screw 20, but only those which are appropriate and sufficient for supporting a specific kind of bone fracture F.

Figure 7A:
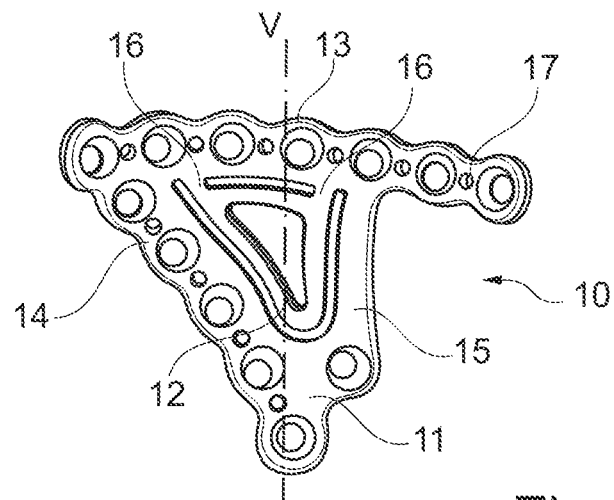
FIG. 7a is a three-dimensional front view of the bone plate implant having an angle of inclination of 0° showing central vertical axis V.
Figure 7B:
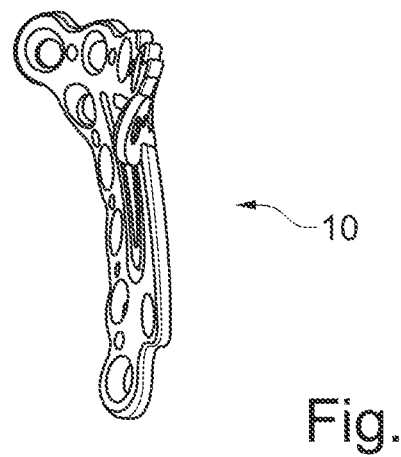
FIG. 7b is a three-dimensional side view of FIG. 7a, wherein the bone plate implant is turned approximately 80° about its vertical central axis V.
Figure 7C:
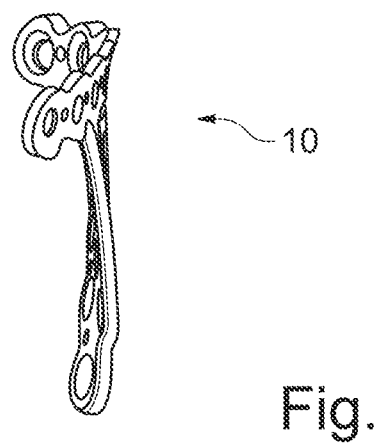
FIG. 7c is a three-dimensional side view of FIG. 7a, wherein the bone plate implant is turned approximately 90° about its vertical central axis V.

FIGS. 7a to 7c are three-dimensional views of the bone plate implant 10 with the flap portion 12 having an angle of inclination $\alpha$ of 0°, viewed from different directions. As can be seen best in FIG. 7c, the bone plate implant 10, or only the outer frame 11 may be twisted about the vertical center axis V. The vertical center axis V of the bone plate implant 10 is the vertical center line in FIG. 7a. In other words, the lower and upper ends of the outer frame portion 11 are rotated in opposite direction about the vertical center axis. Further, the two ends of the pelvis brim segment 13 are bent away from the surface of the bone plate implant supposed to abut to the bone. This way, the pelvic brim segment 13 describes a curve along its longitudinal direction. However, such deformations of the bone plate implant 10, the outer frame 11 and/or the flap portion 12 vary depending on the fracture and the surface of the bone to be buttressed.

Figure 8:
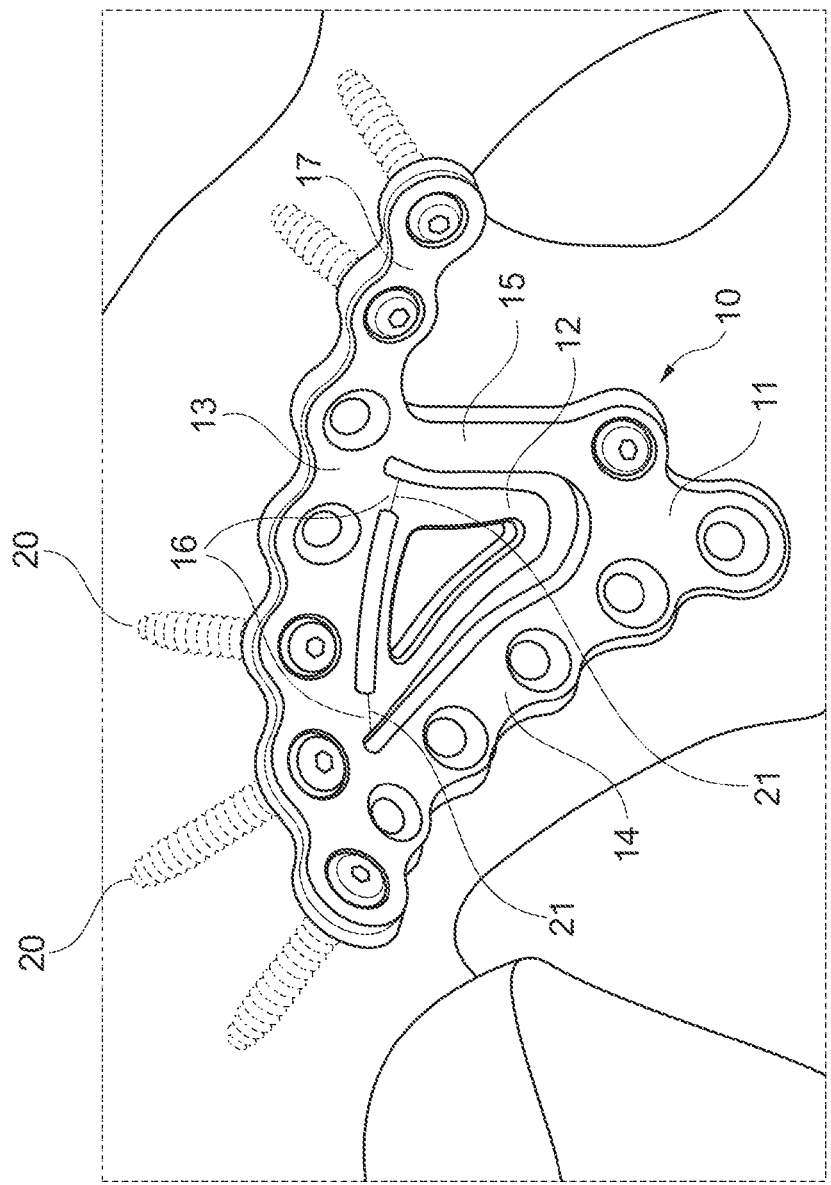
FIG. 8 is a three-dimensional front view of the implanted bone plate implant with the flap portion having an angle of inclination α of 10°.
Figure 9:
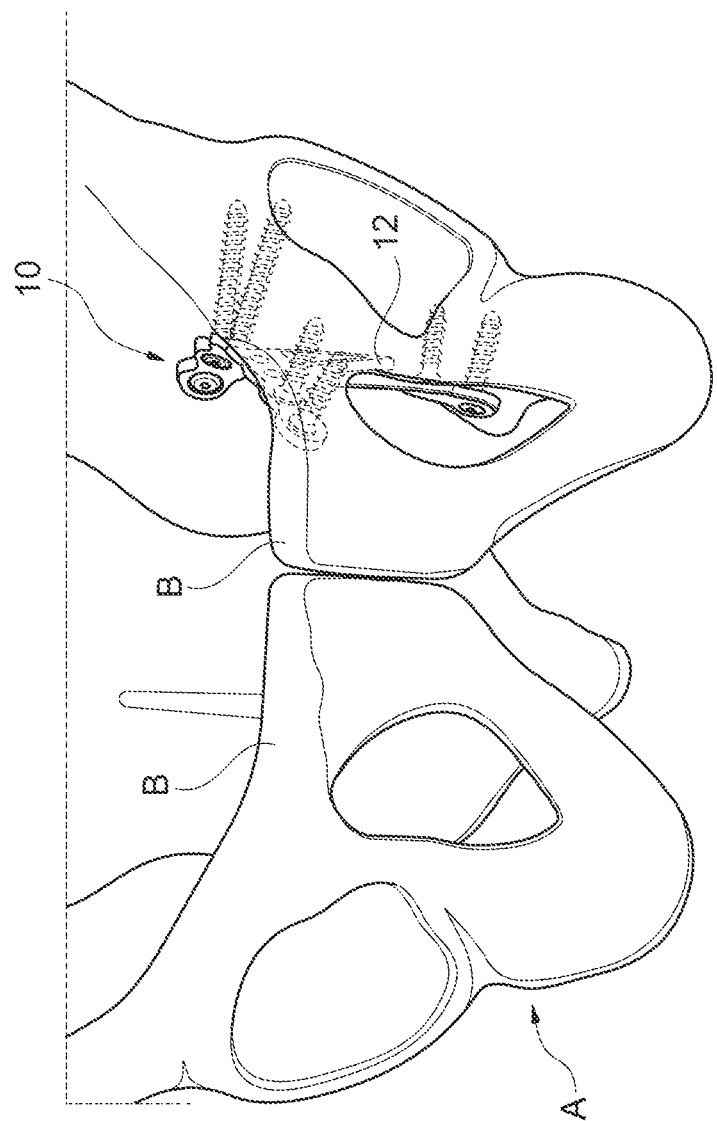
FIG. 9 is a three-dimensional view of the human pelvis with the implanted bone plate implant with the flap portion having an angle of inclination α of 10°, the view is shown from a perspective looking at the front of the human pelvis.
Figure 11A:
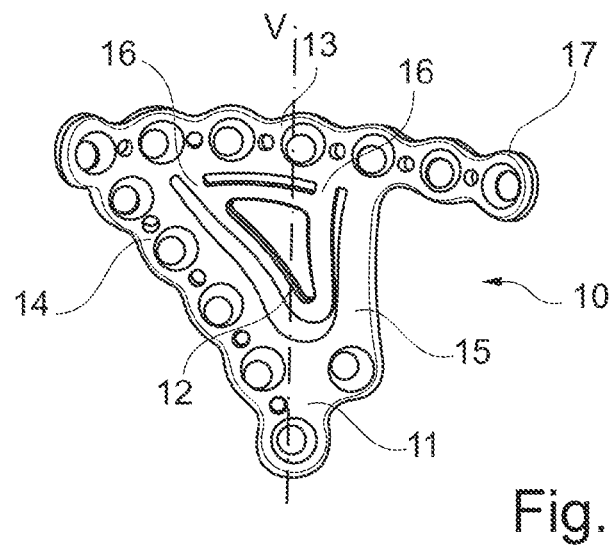
FIG. 11a is a three-dimensional front view of the bone plate implant of FIGS. 8 to 10 with the flap portion having an angle of inclination α of 10°.
Figure 11B:
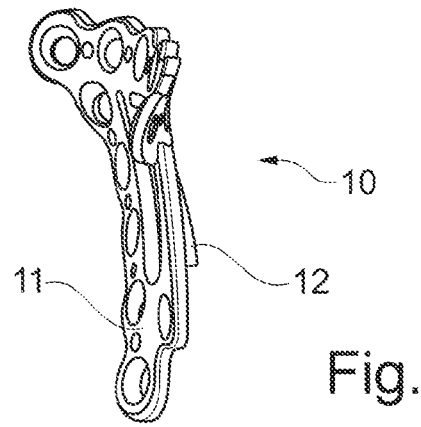
FIG. 11b is a three-dimensional side view of FIG. 11a, wherein the bone plate implant is turned approximately 80° about its vertical central axis V.
Figure 11C:
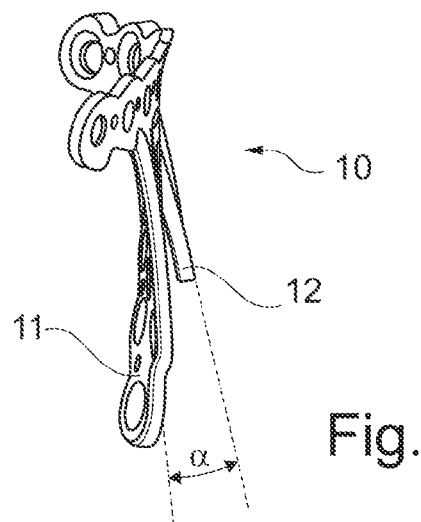
FIG. 11c is a three-dimensional side view of FIG. 11a, wherein the bone plate implant is turned approximately 90° about its vertical central axis V.

FIG. 8 is a three-dimensional view of the implanted bone plate implant 10 with the flap portion 12 having an angle of inclination $\alpha$ of 10°. FIG. 9 is a three-dimensional view of the human pelvis A with the implanted bone plate implant 10 having an angle of inclination $\alpha$ of 10°, the view is shown from a perspective looking at the front of the human pelvis A, and FIG. 10 is an enlarged three-dimensional view of FIG. 9. In FIG. 9, the bone plate implant 10 is shown implanted on the posterior surface of the pelvis adjacent the acetabulum. FIGS. 11a to 11c are three-dimensional views of the bone plate implant 10 with the flap portion 12 having an angle of inclination $\alpha$ of 10°, viewed from different directions. In contrast to the previous Figures, in FIGS. 8 to 11c, the flap portion 12 is positioned with an angle of inclination $\alpha$ of 10° relative to the outer frame portion 11 (angle only indicated in FIG. 11c). Further, in FIG. 8 bending lines 21 are illustrated, which may be formed when the flap portion 12 is bent along the material interconnection 16.

Figure 12A:
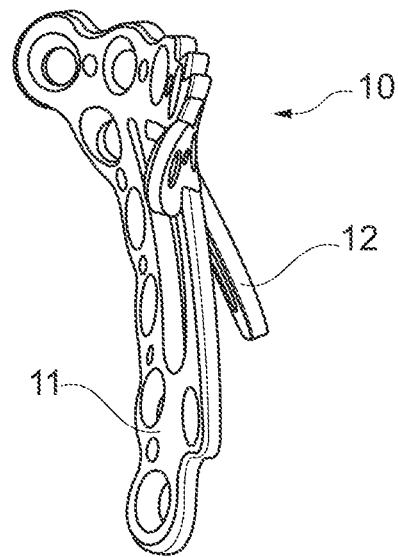
FIG. 12a is a three-dimensional side view of the bone plate implant with the flap portion having an angle of inclination α of 20°, wherein the bone plate implant is turned approximately 80° about its vertical central axis compared to a front view.
Figure 12B:
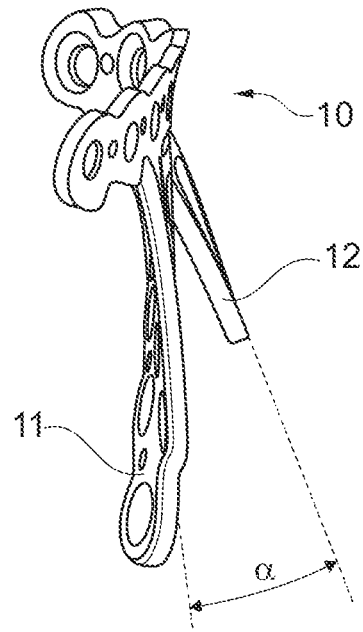
FIG. 12b is a three-dimensional side view of the bone plate implant of FIG. 12a, wherein the bone plate implant is turned approximately 90° about its vertical central axis compared to a front view.

FIGS. 12a and 12c are three-dimensional views of the bone plate implant 10 with the flap portion 12 having an angle of inclination α of 20°, viewed from different directions. In contrast to the previous Figures, in FIGS. 12a and 12b, the flap portion 12 is positioned with an angle of inclination α of 20° relative to the outer frame portion (angle only indicated in FIG. 12b).

The angle of inclination α shown in FIGS. 8 to 12b is formed as described in this specification either by plastic deformation, or according to the below mentioned pre-bending or pre-forming.

As an alternative to the above, the outer frame portion, the flap portion and/or the bone plate implant do not necessarily have to be triangularly shaped, but can also have another shape such as the shape of a quadrangle, a rectangle, a square, etc.

Instead of being formed monolithically, it would also be feasible to form the outer frame portion 11 and the flap portion 12 of different pieces and/or materials with the materials joined together at the material interconnection 16.

The above described plastic deformation is preferably realized solely by hand force without further measures, such as heating of the material before bending, or the like. However, the bone plate implant can also be constructed such that bending tools are necessary and provided for the mentioned plastic deformation. Also, the material can be chosen such that is has to be heated in order to be plastically deformable.

Alternatively to the forming of the outer frame portion 11, the flap portion 12 and/or the material interconnection 16 by hand force, the entire bone plate implant can already be provided in an appropriately pre-bent shape from the manufacturer, which can be realized by manufacturing a flat, planar bone plate implant 10 which is then formed into the appropriate shape by machine bending, wherein the angle of inclination α of the flap portion 12 relative to the outer frame portion 11 is provided by the manufacturer.

As another alternative, the entire bone plate implant can be provided in an appropriately pre-formed shape from the manufacturer, which can be realized by already casting or die cutting the bone plate implant 10 in the appropriate shape, wherein the desired angle of inclination α of the flap portion relative to the outer frame portion 11 is provided by the manufacturer. In this case, optionally the material could be chosen such that it cannot be plastically deformed by hand force.

Figure 13:
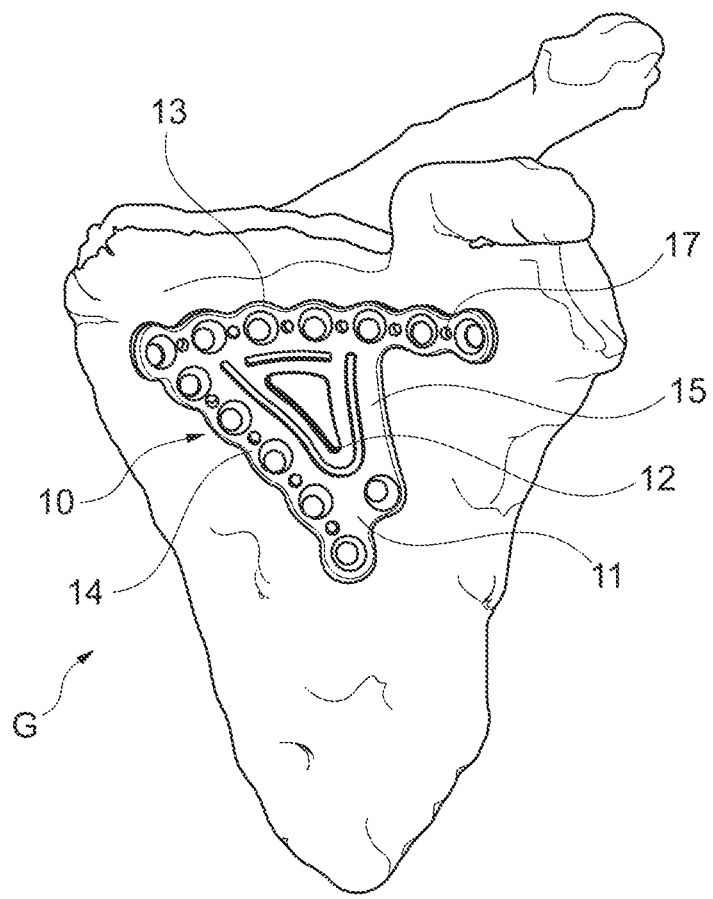
FIG. 13 shows the bone plate of the present invention mounted on a scapula.

Referring to FIG. 13 there is shown a bone plate 10 mounted on the anterior surface (front) of a scapula. This would be used to treat a comminuted fracture of the scapula. The plate is similar in shape (but may be of a different size) as the pelvic plate described in relation to FIGS. 2 to 4.

The method of use of the bone plate will now be described. Preoperatively the surgeon decides whether to use the plate based on the injury/fracture pattern using mainly standard radiographs and CT-scans. Virtual templating can be performed using the 3D-reconstruction of the CT-scans and 3D-models of the plate. Plates of various sizes are available and can be supplied in a kit. Also some planning can be done how to additionally contour the plate and how much pre-bend to add to the flap portion of the plate. Apart from fracture-pattern the amount of this additional spring-loaded force applied through the flexible flap is also influenced by other medical factors such as bone quality or other co-morbidities.

Intra-operatively, the surgeon after achieving adequate fracture reduction, can insert a bending template into the portion of the pelvis where plate placement is planned. These templates are typically very thin/easy to shape to the bone constructs, for example, can be made from a very ductile aluminum alloy less than a millimeter in thickness. Also the plate itself can be held onto the reduced surface to get an impression of the necessary adjustments by checking the fit visually and by feel.

The frame and general shape is then adjusted by the surgeon manually or by using dedicated bending instruments. These plate benders can change the shape of the plates in multiple directions and axis'. Typically the frame will be contoured to the shape of the bone prior to deforming the flap for additional pressure on the fracture site. The flap can be pre-bent by hand or, if that's not possible or insufficient, a dedicated bending instrument can push the flap in the direction of the bone. The amount of flap-deformation is aided by information in the operative technique relating to the properties of a specific size plate. For example, how much of a pre-bend will generate how much spring-force on the fragment. In this way the pre-bend can be adjusted according to special medical considerations.

The implant fit might have to be adjusted after initially trying to place the plate on the bone. This process can be iterative in multiple steps. Whether to utilize the additional inward flap-bending or not and to what degree is a judgment that has to be made by the operating surgeon.

While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously. Any reference signs in the claims should not be construed as limiting the scope of the invention.

The invention claimed is:

1. A bone plate implant comprising:
a frame portion having a surface which can conform to a surface of a bone to which the bone plate implant is to be implanted, the frame portion having a plurality of apertures each for accommodating a bone screw for fixing the bone plate implant to the bone, and
a generally triangular shaped flap portion partially attached to the outer frame portion, the frame portion surrounding the flap portion such that a bone contacting surface of the flap portion is located within an outer boundary of the frame portion,
wherein the flap portion is partially attached to the outer frame portion via a material interconnection and is separated from the frame portion by a continuous slot that partially surrounds the flap portion, and is bent to an angle of inclination with respect to a plane defined by a surface of the frame portion,
wherein the flap portion is adapted to function as a stabilizing and supporting structure for a comminuted area of the bone by applying a stabilizing force to the comminuted area, which stabilizing force is directed transverse to the surface of the frame portion.

2. The bone plate implant according to claim 1, wherein an angle of inclination (α) of the flap portion defining the bending of the flap away from the frame-surface is adjustable relative to the frame-surface by plastically deforming a portion of the material interconnection between the flap portion and the frame portion.

3. The bone plate implant according to claim 2, wherein the flap portion is pre-bent away from the frame portion surface with an angle of inclination (α) relative to the frame-surface.

4. The bone plate implant according to claim 1, wherein the frame portion is plastically deformable.

5. The bone plate implant according to claim 1, wherein the flap portion is plastically deformable.

6. The bone plate implant according to claim 1, wherein the bone plate implant is formed from one piece of material.

7. The bone plate implant according to claim 1, wherein the outer frame portion is a closed frame.

8. The bone plate implant according to claim 1, wherein the flap portion is free of fixation apertures for receiving fastening means.

9. The bone plate implant according to claim 1, wherein the flap portion is connected with the outer frame portion via material bridges.

10. The bone plate implant according to claim 1, wherein the outer frame portion is provided with a projection projecting in a direction in parallel to an imaginary bending axis of the material interconnection.

11. The bone plate implant according to claim 1, wherein the frame portion is substantially triangular.

12. The bone plate implant according to claim 1, wherein the outer shape of the flap portion substantially corresponds to the inner shape of the outer frame portion.

13. The bone plate implant according to claim 1, wherein the material interconnection of the flap portion to the frame portion comprises a spring constant between 200 N/mm and 2400 N/mm.

14. A surgical method for implanting the bone plate implant according to claim 1, comprising the steps of
pre-bending the outer frame portion according to the shape of the bone,
pre-bending the flap portion towards an area of the bone to be buttressed,
implanting the pelvis bone plate implant by fixing it to the bone.

15. The method as set forth in claim 14 wherein the pre-bending of the outer frame portion involves contouring the outer frame portion to the shape of a pelvic or scapular area to which the bone plate implant is to be applied.

16. The method as set forth in claim 15 wherein the flap portion is bent to an angle of inclination with respect to the frame portion between 10° and 20°.

17. A method for fixing a fracture of a pelvic or scapular bone comprising: determining the size and location of a fractured bone area;
obtaining a bone plate implant of appropriate size comprising:
a frame portion having a plurality of apertures, each for accommodating a bone screw for fixing the bone plate implant to a bone, and a surface which can conform to a surface of a bone to which the bone plate implant is to be implanted;
a generally triangular shaped flap portion partially attached to the outer frame portion, the frame portion surrounding the flap portion such that a bone contacting surface of the flap portion is located within an outer boundary of the frame portion;
wherein the flap portion is partially attached to the outer frame portion via a material interconnection and is separated from the frame portion by a continuous slot that partially surrounds the flap portion, and is bent to an angle of inclination with respect to a plane defined by a surface of the frame portion;
wherein the flap portion is adapted to function as a stabilizing and supporting structure for a comminuted area of the bone by applying a stabilizing force to the comminuted area, which stabilizing force is directed transverse to the surface of the frame portion;
reducing the fractured bone;
determining the shape of the reduced fractured bone area;
bending the flap portion in a direction away from the frame;
conforming the frame portion of the bone plate to generally match the shape of the reduced fractured bone area; and
mounting the bone plate frame on the fracture in a manner which deflects the flap portion towards the frame.

18. The method as set forth in claim 17 wherein the flap portion is bent to an angle of inclination with respect to the frame portion between 10° and 20°.

19. The method as set forth in claim 17 wherein the shape of the reduced fractured bone area is determined by a bendable template.

20. A bone plate implant comprising:
a frame having first, second and third frame portions, each having a bone contacting surface, the first frame portion having a plurality of fixation apertures each for accommodating a bone screw, the second and third frame portions connected to the first frame portion at first and second attachment areas; and
a generally triangularly shaped flap portion attached to the first frame portion at a third and fourth attachment areas intermediate the first and second attachment areas, the flap portion surrounded by the second and third frame portions, the flap portion is separated from the second and third frame portions by a continuous slots, and a slot separating the flap from the first frame portion is located intermediate the third and fourth attachment areas, the flap portion being free of fixation apertures.

21. The bone plate as set forth in claim 20, wherein the flap portion has a bone contacting surface capable of being spaced outwardly of the bone contacting surfaces of the first, second and third frame portions.

22. The bone plate as set forth in claim 21, wherein the generally triangular shaped flap portion has a generally triangular shaped central opening.

* * * * *